United States Patent [19]

Pless et al.

[11] Patent Number: 4,949,719
[45] Date of Patent: Aug. 21, 1990

[54] METHOD FOR CARDIAC DEFIBRILLATION

[75] Inventors: Benjamin Pless, Menlo Park; Phillip L. Ball, San Jose, both of Calif.

[73] Assignee: Ventritex, Inc., Sunnyvale, Calif.

[21] Appl. No.: 344,011

[22] Filed: Apr. 26, 1989

[51] Int. Cl.$^5$ ............................................. A61N 1/39
[52] U.S. Cl. ......................... 128/419 D; 128/419 PG
[58] Field of Search ......... 128/419 D, 419 PG, 419 P

[56] References Cited

U.S. PATENT DOCUMENTS

| | | | |
|---|---|---|---|
| 3,805,795 | 4/1974 | Denniston et al. | 128/419 D |
| 4,384,585 | 5/1983 | Zipes | 128/419 D |
| 4,473,078 | 9/1984 | Angel | 128/419 D |
| 4,572,191 | 2/1986 | Mirowski et al. | 128/419 D |
| 4,592,367 | 6/1986 | Imran | 128/419 D |
| 4,614,192 | 9/1986 | Imran et al. | 128/419 D |
| 4,619,265 | 10/1986 | Morgan et al. | 128/419 D |

*Primary Examiner*—Lee S. Cohen
*Assistant Examiner*—Kennedy J. Schaetzle
*Attorney, Agent, or Firm*—Gerstman & Ellis, Ltd.

[57] ABSTRACT

A method for cardiac defibrillation is described, for use with an implanted defibrillator. A patient's R-waves are sensed to detect the R-R intervals. If an arrhythmia is detected, the charging of a capacitor is commenced. Determinations are made whether the arrhythmia is still in progress and whether the capacitor is charged a predetermined amount. If the arrhythmia is not still in progress, the charging is discontinued. If the arrhythmia is still in progress and the capacitors are charged a predetermined amount, another R-R interval is detected and if the R-R interval is shorter than a selected amount, a shock is delivered to the heart.

14 Claims, 4 Drawing Sheets

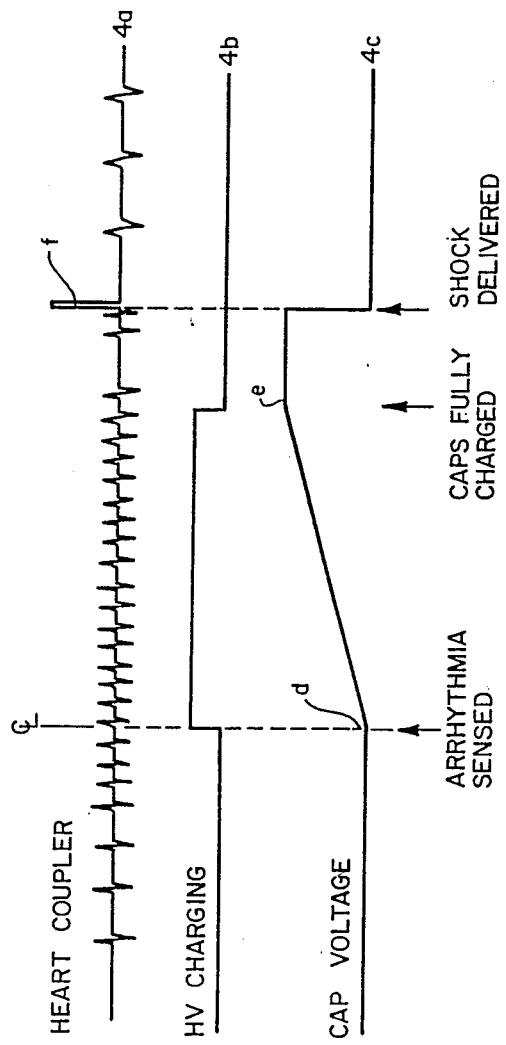

METHOD FOR CARDIAC DEFIBRILLATION

FIELD OF THE INVENTION

The present invention concerns a novel method for safely defibrillating the heart using an implanted cardiac defibrillator.

BACKGROUND OF THE INVENTION

Implanted cardiac defibrillators are known, in which the high voltage capacitors are discharged to provide a defibrillating high energy shock that is timed off the sensed electrogram. However, if there is a mistaken diagnosis by the device and the shock is delivered into sinus, it is particularly arrhythmogenic if it is asynchronous and happens to coincide with the vulnerable zone. Further, if the rhythm converts back to sinus rhythm, we have found that the shock should be aborted since even a synchronous shock carries some risk.

Present implantable defibrillators that are sold by CPI/Intec are committed to deliver a high voltage shock once the capacitors begin charging. Thus after charging is completed, the high voltage shock will necessarily be delivered. Likewise, the implantable cardioverter that was sold by Medtronic, Inc. was also committed to deliver the high voltage shock once the capacitors begin charging.

In the implantable defibrillator presently sold by Telectronics, Inc., during charging of the capacitors the charging is discontinued part way to recheck the arrhythmia status. However, independent of the result of that arrhythmia check, the capacitors continue charging and an arrhythmia check is made again when the capacitors are fully charged. Only if both checks show an arrhythmia, do the capacitors deliver the high voltage shock to the heart.

It is an object of the invention to provide a cardiac defibrillation method in which the high voltage shock does not coincide with the vulnerable zone.

Another object of the present invention is to provide a cardiac defibrillation method in which the high voltage shock is aborted if the arrhythmia converts back to sinus rhythm.

Other objects and advantages of the invention will become apparent as the description proceeds.

SUMMARY OF THE INVENTION

In accordance with the present invention, a method is provided for cardiac defibrillation with an implanted defibrillator having means for sensing R-waves, energy storage means, charging means and discharging means for delivering a shock to the heart. The method of the present invention comprises the steps of: sensing a patient's R-waves to detect R-R intervals; if an arrhythmia is detected, then commencing charging of the storage means; determining whether the arrhythmia is still in progress; if the arrhythmia is still in progress, then determining if the storage means is charged a predetermined amount; if the storage means is charged a predetermined amount, then detecting at least another R-R interval; and only if another R-R interval is shorter than a selected amount before sinus rhythm is redetected, then delivering a shock to the heart.

In accordance with the method of the present invention, the shock is delivered to the heart substantially immediately following the sensing of an R-wave after a short (i.e., arrhythmia) interval.

A more detailed explanation of the invention is provided in the following description and claims, and as illustrated in the following drawings.

BRIEF DESCRIPTION OF THE DRAWINGS

FIG. 4 is a timing diagram of a still further operation thereof.

FIG. 5 is a flow chart of a method in accordance with the principles of the present invention.

DETAILED DESCRIPTION OF THE ILLUSTRATIVE EMBODIMENT

Figure 1:
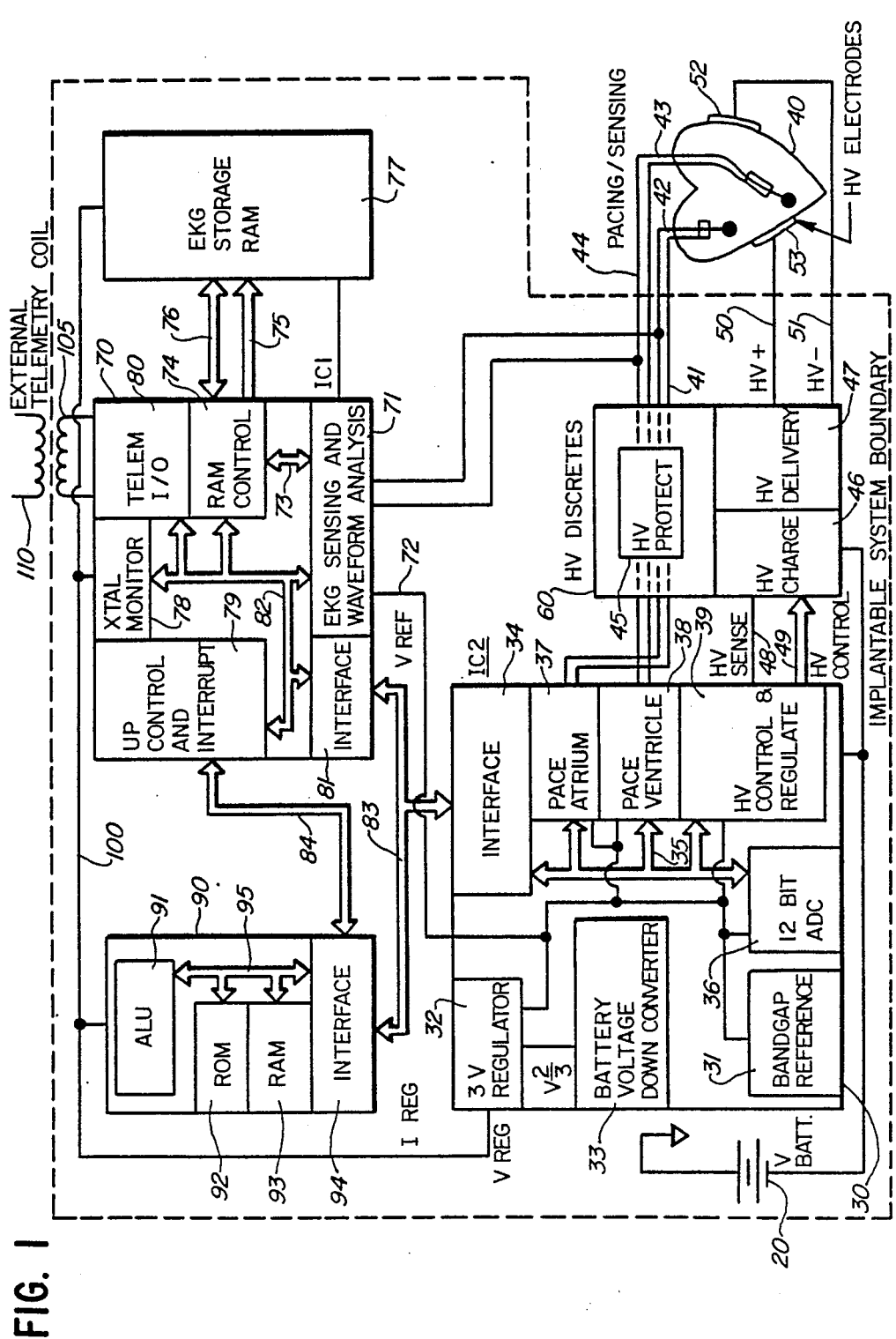
FIG. 1 is a block diagram of an implantable defibrillator constructed in accordance with the principles of the present invention.

Referring to FIG. 1, the block diagram for the implantable defibrillator includes four ICs and a set of high voltage discretes. The battery produces a positive voltage with respect to ground that varies from about 6.4 volts when new, to 5.0 volts at the end of service. The battery directly powers IC2 30 and the high voltage discretes 60.

IC2 contains a band-gap reference circuit 31 that produces 1.235 volts, and 3 volt regulator that powers the microprocessor 90, IC1 70, and the ECG storage RAM 77 through line 100. The 3 volt regulator runs off of a switched capacitor V ⅔ battery voltage down converter 33 for improved efficiency.

The microprocessor 90 communicates with IC2 through a data and address bus 83 and an on-chip interface 34 that contains chip-select, address decoding and data bus logic as is typically used with microprocessor peripherals. The internal bus 35 allows the microprocessor to control a general purpose ADC 36, the atrial pace circuits 37, the ventricular pace circuits 38, and the HV control and regulate block 39.

The ADC 36 is used by the microprocessor to measure the battery and other diagnostic voltages within the device.

The atrial pace circuits 37 include a DAC that provides the ability to pace at regulated voltages. It communicates with the atrium of a heart 40 through two lines. One line 41 is a switchable ground; the other line 42 is the pacing cathode and is also the input to the atrial sense amplifier, as will be described below.

The ventricular pace circuits 37 include a DAC that provides the ability to pace at regulated voltages. It communicates with the ventricle of a heart 40 through two lines. One line 43 is a switchable ground; the other line 44 is the pacing cathode and is also the input to the ventricular sense amplifier, as will be described below.

Both the atrial and ventricular pace lines pass through high voltage protection circuits 45 to keep the defibrillation voltages generated by the device from damaging the pacing circuits 37 and 38.

The HV control and regulate block 39 on IC2 30 is used by the microprocessor 90 to charge a high voltage capacitor included in the HV charge block 46 to a regulated voltage, and then to deliver the defibrillating pulse to the heart 40 through the action of switches in the HV delivery block 47. An HV sense line 48 is used by the HV regulation circuits 39 to monitor the defibrillating voltage during charging. An HV control bus 49 is used by the HV control circuits 39 to control the switches in the HV delivery block 47 for delivering the defibrillating pulse to the electrodes 52, 53 through lines 50 and 51.

IC1 70 is another microprocessor peripheral and provides timing, interrupt, telemetry, ECG storage, and sensing functions.

A dual channel electrogram sensing and waveform analysis section 71 interfaces with the atrium and ventricle of the heart 40 through lines 42 and 44 respectively. The sensed electrogram is amplified and digitized. The amplifiers contained in this section 71 have multiple gain settings that are under microprocessor control for maintaining an AGC. Features such as peak voltage and complex width are extracted by the waveform analysis circuits 71 for the microprocessor 90 to use in discriminating arrhythmias from normal sinus rhythm. The voltage reference 31 from IC2 30 is used by the digitizer circuit 71 in the usual fashion, and is supplied by line 72.

The digitized ECG is provided to the RAM controller 74 through a bus 73. The RAM controller sequences through the addresses of a static RAM 77 to maintain a pretrigger area, and this produces a post trigger area upon command from the microprocessor 90.

The crystal and monitor block 78 has a 100 KHz crystal oscillator that provides clocks to the entire system. The monitor is a conventional R-C oscillator that provides a back-up clock if the crystal should fail.

The microprocessor communicates with IC1 through two buses, 83 and 84. One bus 83 is a conventional data and address bus and goes to an on-chip interface 81 that contains chip select, address decoding and data bus drivers as are typically used with microprocessor peripherals. The other bus 84 is a control bus. It allows the microprocessor to set up a variety of maskable interrupts for events like timer timeouts, and sense events. If an interrupt is not masked, and the corresponding event occurs, an interrupt is sent from IC1 70 to the microprocessor 90 to alert it of the occurrence. On IC1 70, the up control and interrupt section 79 contains microprocessor controllable timers and interrupt logic.

The device can communicate with the outside world through a telemetry interface 80. A coil 105 is used in a conventional fashion to transmit and receive pulsed signals. The telemetry circuits 80 decode an incoming bit stream from an external coil 110 and hold the data for subsequent retrieval by the microprocessor 90. When used for transmitting, the circuit 80 receives data from the microprocessor 90, encodes it, and provides the timing to pulse the coil 105. The communication function is used to retrieve data from the implanted device, and to change the modality of operation if required.

The microprocessor 90 is of conventional architecture comprising an ALU 91, a ROM 92, a RAM 93, and interface circuits 94. The ROM 92 contains the program code that determines the operation of the device. The RAM 93 is used to modify the operating characteristics of the device as regards modality, pulse widths, pulse amplitudes, and so forth. Diagnostic data is also stored in the RAM for subsequent transmission to the outside world. The Algorithmic Logic Unit (ALU) 91 performs the logical operations directed by the program code in the ROM.

The program code is written to perform certain desirable functions which are best described in flowchart form.

Figure 2:
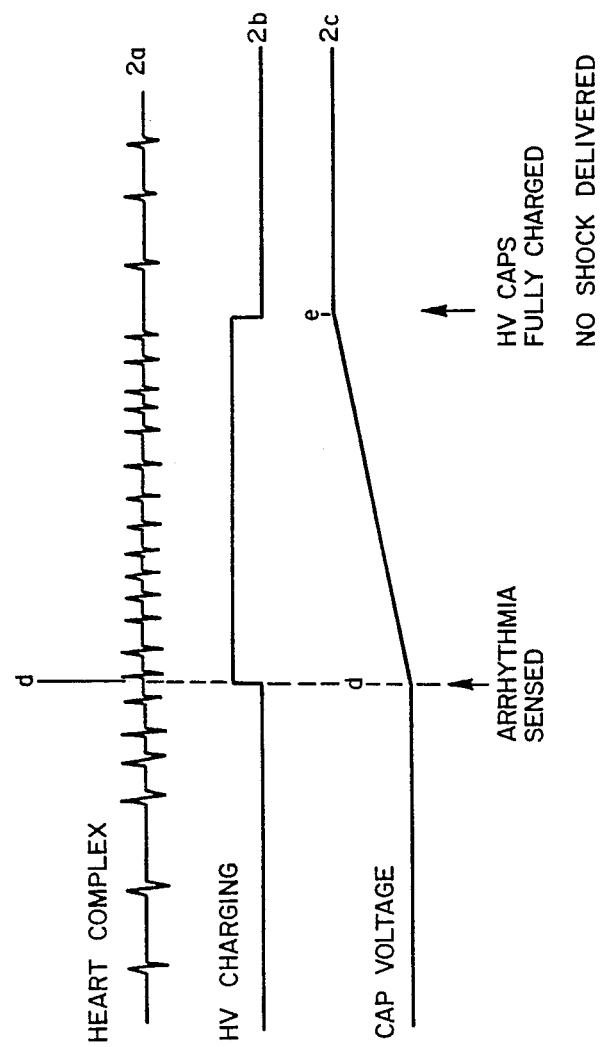
FIG. 2 is a timing diagram of an operation thereof.

Referring now to FIG. 2, waveform 2a represents the heart complex. It is illustrated starting off in sinus rhythm and then speeding up to a tachycardia at point d. Waveform 2b, the high voltage charging status indicator waveform, is a digital level that represents the high voltage charging. Waveform 2c is the master voltage which increases to point e, the point when the capacitors are fully charged and the high voltage charge automatically discontinues. However, it can be seen that at point e the arrhythmia ceased and there are no further short intervals. Thus no shock is delivered.

Figure 3:
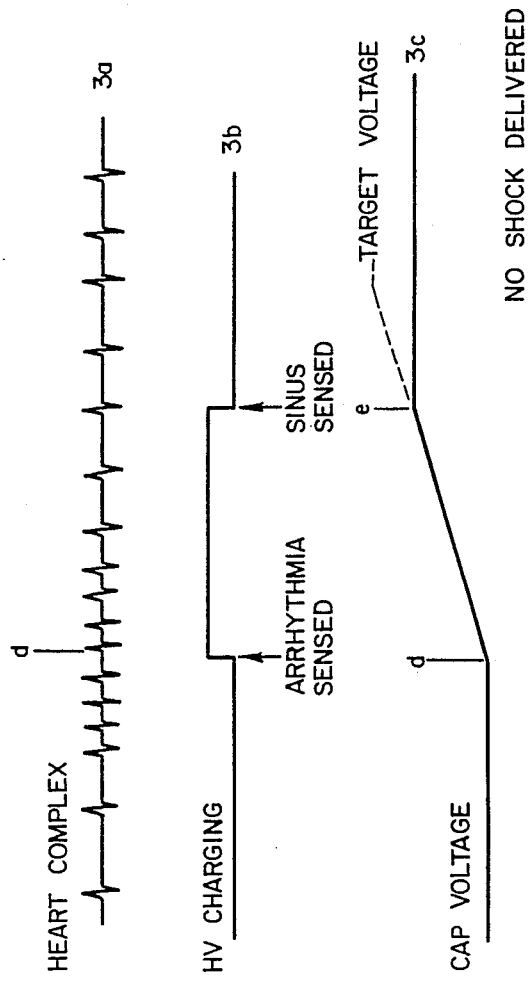
FIG. 3 is a timing diagram of another operation thereof.

Referring to FIG. 3, heart complex waveform 3a commences with sinus rhythm and accelerates to a tachycardia at point d. The arrhythmia is sensed and the high voltage charging status line 3b goes high. However, the device continues to sense while charging is commencing and since the heart complex returned to sinus rhythm during charging, this is detected and the capacitor charging is terminated at point e even though the target voltage is not reached. In this case, no shock is delivered because the rhythm returned to sinus during the charging of the capacitor.

Referring now to FIG. 4, heart complex trace 4a commences in sinus rhythm but speeds up to a tachycardia at point d. The arrhythmia is sensed, high voltage charging line 4b goes high and stays high until the capacitors are fully charged as indicated on capacitor voltage line 4c, point e. High voltage charging line 4b goes low at point e and at this point the device is trying to synchronize and waits for the next R-wave. After receiving the next R-wave, it awaits the next R-wave, and it determines that there is a long interval so the shock is not delivered. Thereafter, however, there is a short interval and the shock f is delivered to the heart.

A flowchart illustrating the method described with respect to time and timing diagrams is illustrated in FIG. 5. FIG. 5 illustrates the ventricular shock synchronizing procedure. First, the next R-wave is awaited 120. When the R-wave is sensed, the system checks to see if an arrhythmia is still in progress 122. If not, the capacitor charging is discontinued 124 and the routine is exited 126.

If the arrhythmia is still in progress 122, the high voltage circuit is polled 128 to determine if the capacitors are fully charged 130. If the capacitors are not fully charged, return via 132 to the top of the loop and await the next R-wave 120. If the capacitors are fully charged, wait for one R-wave 134 and wait for another R-wave 136 and then a determination is made whether or not the interval between those two R-waves is short 138. If the interval was long, then verify whether or not the arrhythmia is still in progress 140. If the arrhythmia is not still in progress, then exit from the routine 142. If the arrhythmia is still in progress, then return to waiting for another R-wave 136. If a next R-R interval is now short, then a high voltage shock is delivered to the heart 144 and the routine is exited 146.

It can be seen that a novel method has been shown and described for cardiac defibrillation, in which a detected arrhythmia is checked during charging of the capacitors and the charging is discontinued if termination of the arrhythmia is detected. If charging is completed, however, a high voltage shock is not delivered on the first sensed event after completion of charging. Further, even if charging is completed, a high voltage shock is not delivered if the previous sense events were of long interval. This minimizes the amount of high voltage charging that is necessary, with an associated decrease in battery usage. Further, it most effectively reduces the probability of delivering a shock into sinus rhythm.

Although an illustrative embodiment of the invention has been shown and described, it is to be understood that various modifications and substitutions may be made by those skilled in the art without departing from the novel spirit and scope of the present invention.

What is claimed is:

1. A system for cardiac defibrillation which comprises:
    an implanted defibrillator having means for sensing R-waves;
    energy storage means;
    charging means for charging the energy storage means;
    discharging means for discharging the energy storage means and delivering a shock to the heart;
    means for measuring R-R intervals from said sensed R-waves;
    means for commencing charging of said storage means if an arrhythmia is detected;
    means for determining whether the arrhythmia is still in progress;
    means for discontinuing the charging if the arrhythmia is not still in progress;
    means for detecting another R-R interval if said storage means is charged a predetermined amount; and
    said discharging means delivering said shock to the heart if said another R-R interval is shorter than a selected amount.

2. A system as described in claim 1, including means for determining if said storage means is charged a predetermined amount if said arrhythmia is still in progress.

3. A method for cardiac defibrillation with an implanted defibrillator having means for sensing R-waves, energy storage means, charging means and discharging means for delivering a shock to the heart, which method comprises the steps of:
    sensing a patient's R-waves to detect R-R intervals;
    if an arrhythmia is detected, then commencing charging of said storage means;
    determining whether the arrhythmia is still in progress;
    if said arrhythmia is still in progress, then determining if said storage means is charged a predetermined amount;
    if said storage means is charged, said pre-determined amount, then detecting another R-R interval;
    if said another R-R interval is shorter than a selected amount, then delivering a shock to the heart.

4. A method as described in claim 3, including the step of discontinuing the charging if said arrhythmia is not still in progress.

5. A method as described in claim 3, in which said shock is delivered to the heart substantially immediately following the sensing of an R-wave.

6. A method as described in claim 3, wherein if said storage means is not charged said predetermined amount, then continuing to determine whether the arrhythmia is still in progress; and discontinuing the charging if the arrhythmia is not still in progress.

7. A method as described in claim 3, wherein if said another R-R interval is not shorter than said predetermined amount, then:
    determining whether the arrhythmia is still in progress; if said arrhythmia is still in progress then detecting another R-wave, determining whether the last R-R interval was shorter than a selected amount, and delivering a shock to the heart if said last R-R interval was shorter than a selected amount.

8. A method as described in claim 7, wherein if said arrhythmia is not still in progress, then inhibiting the shock to the heart.

9. A method for cardiac defibrillation with an implanted defibrillator having means for sensing R-waves, energy storage means, charging means and discharging means for delivering a shock to the heart, which method comprises the steps of:
    sensing a patient's R-waves to detect R-R intervals;
    if an arrhythmia is detected, then commencing charging of said storage means;
    determining whether the arrhythmia is still in progress;
    if said arrhythmia is not still in progress, then discontinuing the charging;
    if said arrhythmia is still in progress, then determining if said storage means is charged a predetermined amount;
    if said storage means is charged said predetermined amount, then detecting another R-R interval;
    if said another R-R interval is shorter than a selected amount, then delivering a shock to the heart;
    if said another R-R interval is not shorter than a predetermined amount, then determining whether the arrhythmia is still in progress;
    if said arrhythmia is still in progress then detecting another R-wave, determining whether the previous R-R interval was shorter than a selected amount, and delivering a shock to the heart if said previous R-R interval was shorter than a selected amount; and
    if said arrhythmia is not still in progress, then inhibiting the delivery of a shock to the heart.

10. A method as described in claim 9, wherein:
    if said storage means is not charged said predetermined amount, then continuing to determine whether the arrhythmia is still in progress; and
    if the arrhythmia is not still in progress, then discontinuing the charging.

11. A method for cardiac defibrillation with an implanted defibrillator having means for sensing R-waves, energy storage means, charging means and discharging means for delivering a shock to the heart, which method comprises the steps of:
    sensing a patient's R-waves to detect R-R intervals;
    if an arrhythmia is detected, then commencing charging of said storage means;
    determining whether the arrhythmia is still in progress;
    if said arrhythmia is still in progress, then determining if said storage means is charged a predetermined amount;
    if said storage means is charged said predetermined amount, then detecting another R-R interval;
    if said another R-R interval is shorter than a selected amount, then delivering a shock to the heart; and
    if said another R-R interval is not shorter than a predetermined amount, then determining whether the arrhythmia is still in progress; if said arrhythmia is still in progress then detecting another R-wave, determining whether the last R-R interval was shorter than a selected amount, and delivering a shock to the heart if said last R-R interval was shorter than a selected amount.

12. A method as described in claim 11, including the step of discontinuing the charging if said arrhythmia is not still in progress.

13. A method as described in claim 11, wherein if said storage means is not charged said predetermined amount, then continuing to determine whether the arrhythmia is still in progress, and discontinuing the charging if the arrhythmia is not still in progress.

14. A method as described in claim 11, wherein if said arrhythmia is not still in progress, then inhibiting the delivery of a shock to the heart.

* * * * *